(12) United States Patent
Tegels

(10) Patent No.: US 9,307,966 B2
(45) Date of Patent: Apr. 12, 2016

(54) VASCULAR CLOSURE DEVICE ANCHOR

(75) Inventor: Zachary J. Tegels, Minneapolis, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 533 days.

(21) Appl. No.: 13/586,777

(22) Filed: Aug. 15, 2012

(65) Prior Publication Data

US 2014/0052171 A1 Feb. 20, 2014

(51) Int. Cl.
*A61B 17/08* (2006.01)
*A61B 17/00* (2006.01)

(52) U.S. Cl.
CPC ... *A61B 17/0057* (2013.01); *A61B 2017/00004* (2013.01); *A61B 2017/00526* (2013.01); *A61B 2017/00654* (2013.01); *A61B 2017/00659* (2013.01); *A61B 2017/00663* (2013.01); *A61B 2017/00831* (2013.01); *A61B 2017/00964* (2013.01)

(58) Field of Classification Search
CPC ....................................................... A61B 17/08
USPC ................................. 606/213, 151, 144, 214
See application file for complete search history.

(56) References Cited

U.S. PATENT DOCUMENTS

| | | | |
|---|---|---|---|
| 6,045,569 A | 4/2000 | Kensey et al. | |
| 6,090,130 A | 7/2000 | Nash et al. | |
| 6,786,915 B2 * | 9/2004 | Akerfeldt | A61B 17/0057 606/213 |
| 7,618,436 B2 | 11/2009 | Forsberg | |
| 7,749,248 B2 | 7/2010 | White et al. | |
| 7,837,705 B2 | 11/2010 | White et al. | |
| 7,931,670 B2 | 4/2011 | Fiehler et al. | |
| 2002/0198562 A1 | 12/2002 | Akerfeldt et al. | |
| 2003/0009180 A1 * | 1/2003 | Hinchliffe et al. | 606/144 |
| 2009/0210004 A1 | 8/2009 | McGuckin, Jr. et al. | |
| 2009/0216267 A1 * | 8/2009 | Willard et al. | 606/213 |
| 2012/0022585 A1 | 1/2012 | Atanasoska et al. | |

FOREIGN PATENT DOCUMENTS

WO 9529635 A1 11/1995

OTHER PUBLICATIONS

PCT International Search Report for International Application No. PCT/US2013/051043, mailed Dec. 2, 2013 (5 pp.).

* cited by examiner

*Primary Examiner* — Vy Bui
(74) *Attorney, Agent, or Firm* — Holland & Hart

(57) ABSTRACT

A bioresorbable anchor for deployment in a live body, in one embodiment the anchor comprises an inner anchor made of a first bioresorbable material and an outer anchor made of a second bioresorbable material, wherein the outer anchor envelops the inner anchor. In another embodiment, the anchor comprises a base anchor made of a first bioresorbable material and a second bioresorbable material overlays at least a portion of the base anchor. The first bioresorbable material has a faster resorption rate than the second bioresorbable material. Further, the second bioresorbable material can provide additional strength to the anchor structure. A tissue puncture closure device comprising a filament extending from a first end of the closure device to a second end of the closure device; an anchor comprising a plurality of bioresorbable materials; a sealing plug slidingly attached to the filament adjacent to the anchor; and a tamping assembly.

17 Claims, 9 Drawing Sheets

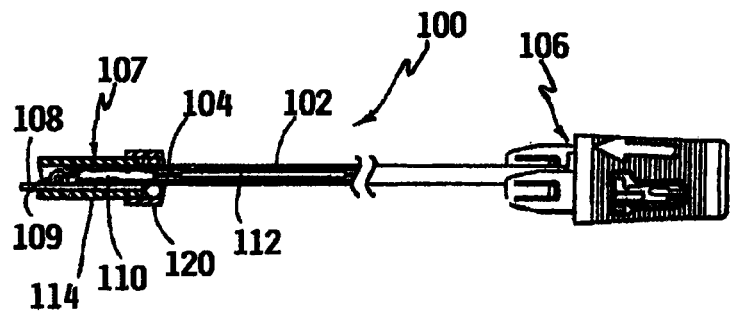
FIG. I (PRIOR ART)
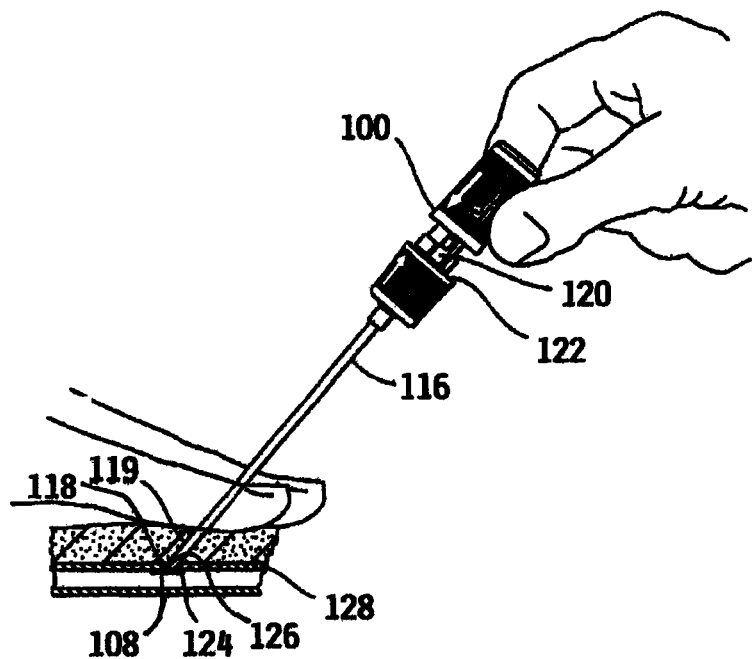
FIG. 2 (PRIOR ART)

VASCULAR CLOSURE DEVICE ANCHOR

FIELD OF THE DISCLOSURE

This disclosure relates generally to medical devices and, more particularly, to anchors used with a device for sealing punctures or internal tissue incisions.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath can be placed in the artery and thereafter instruments (e.g., a catheter) can pass through the sheath and to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,045,569; 6,090,130; 7,618,436; 7,749,248; 7,837,705; 7,931,670; and, and related patents and patent applications, all of which are hereby incorporated by reference.

As noted above, vascular closure devices and processes associated therewith are commonly used to seal arteriotomies such as the ones created when the femoral artery is deliberately punctured in order to perform a procedure. The femoral artery is often punctured in order to clear blockages or obstructions in the patient's circulatory system. The above-mentioned patents describe embodiments of a puncture closure device in which an anchor is inserted through the arteriotomy and positioned against an interior wall of the artery. A sealant plug, such as a collagen sponge, is positioned at an exterior wall of the artery above the arteriotomy. The anchor and collagen sponge are then sandwiched or compressed together to facilitate rapid hemostasis and sealing of the arteriotomy. The anchor, positioned at an internal portion of the incision or opening, seals an internal side of the incision. Preferably, the anchor does not bend or weaken during the implantation process or until after a preferred time after implantation. After a certain period of time, the wound or incision heals, also during which time the anchor is reabsorbed.

The anchor is made of a biologically resorbable material, as the anchor is designed to resorb in the body. Generally, the material composing the anchor is chosen for the resorbtion time of the material in the body, as well as the strength of the material to fulfill the anchor function. A material that provides the bioresorbability that is desired in the anchor may not provide the initial strength that is required in the anchor. Alternately, a material that may provide the strength that is required in the anchor may not provide the rate of resorbtion that is desired. Further, greater control over the resorbtion rate may be desired, as the wound or incision heals. Accordingly, there is a need for improving the anchor, to provide the desired initial strength and resorbability rate.

SUMMARY

The present disclosure contemplates an anchor for a vascular closure device or tissue closure device that is configured to be resorbed by the body within a set desired period of time, and has the strength to perform the function of part of a tissue puncture or incision seal.

In one aspect of the disclosure, an anchor for deployment in a live body is made of a bioresorbable material. The anchor comprises an inner anchor and an outer anchor, where the outer anchor envelopes the inner anchor. The inner anchor is made of a bioresorbable material with a more rapid bioresorption rate than the outer anchor material. The material of the outer anchor can be overmolded on the inner anchor or, alternatively, the material of the outer anchor can be coated on the material of the inner anchor.

In another aspect of the disclosure, an anchor for deployment in a live body is made of a bioresorbable material. The anchor comprises an inner anchor and an outer anchor, where the outer anchor envelopes the inner anchor. The inner anchor is made of a bioresorbable material with a different bioresorption rate than the outer anchor material. The material of the outer anchor can be overmolded on the inner anchor or, alternatively, the material of the outer anchor can be coated on the material of the inner anchor.

In yet another aspect of the disclosure, an anchor for deployment in a live body is made of bioresorbable material. The anchor comprises an inner anchor and an outer anchor, where the outer anchor envelopes the inner anchor. In one aspect, the outer anchor is made of less hydrophilic bioresorbable material than the inner anchor material. The material of the outer anchor can be overmolded on the inner anchor or, alternatively, the material of the outer anchor can be coated on the material of the inner anchor.

In yet another aspect of the disclosure, an anchor for deployment in a live body is made of a bioresorbable material. The anchor comprises a base anchor wherein portions of the base anchor are overmolded or coated with another material. The overmold material or coating material can have a different resorption rate, as compared to the base anchor material. Further, the overmold or coating material can be less hydrophilic than the base anchor material. In addition, the overmold material or the coating material can provide additional strength to the base anchor in the areas of the anchor where the overmold material or coating material has been added to the exterior of the base anchor.

In the various aspects of the disclosure, described above, the overmold material or the coating material can provide additional strength to the anchor. The nature of the inner anchor material and the overmold material or coating material provides the ability to tailor the resorbtion rate of the anchor to meet particular needs. In one aspect, the anchor can be formed using an injection-mold process, where the inner anchor is injection-molded in the first shot, and the outer anchor is molded on the inner anchor in the second shot. If only certain portions of the anchor are to be overmolded, the overmold material can be removed from a completely overmolded inner anchor, or only certain portions of the inner anchor are overmolded. Alternatively, in some aspects of the disclosure, the anchor can be formed by coating the inner anchor. The inner anchor can be coated using spray coating, spin coating, dip coating, thin film coating, vapor deposition coating, or other MEMS techniques.

According to another aspect of the disclosure, there is disclosed a tissue puncture closure tool for partial insertion into and sealing of an internal tissue wall puncture. The tissue closure tool includes a filament extending from a first end of the closure tool to a second end of the closure tool, an anchor for insertion through the tissue wall puncture attached to the filament at the second end of the closure tool, a sealing plug slidingly attached to the filament adjacent to the anchor, and a compaction device adjacent to the sealing plug for advancing the sealing plug toward the anchor. The anchor can be made of a plurality of materials, wherein the materials can have different resorption rates. The anchor can comprise an inner anchor and an outer anchor, where the inner anchor material has a faster resorption rate than the outer anchor material. The outer anchor material can be less hydrophilic than the inner anchor material. The outer anchor material can be overmolded or coated onto the inner anchor material, enveloping the inner anchor. In some aspects, the outer anchor material can be overmolded or coated on portions of the inner or base anchor material, leaving some portions of the inner or base anchor uncoated/not overmolded. Further, the outer anchor material can provide additional strength to the anchor; to the entire anchor if the anchor is completely overmolded or coated with the outer anchor material, or only to the portions of the anchor with outer anchor material.

The above summary of the various representative embodiments of the disclosure is not intended to describe each illustrated embodiment or every implementation of the disclosure. Rather, the embodiments are chosen and described to that others skilled in the art may appreciate and understand the principles and practices of the disclosure. The figures in the detailed description that follows more particularly exemplify these embodiments.

BRIEF DESCRIPTION OF THE DRAWINGS

These as well as other objects and advantages of this disclosure will be more completely understood and appreciated by referring to the following more detailed description of the example embodiments of the disclosure in conjunction with the accompanying drawings of which:

FIG. 1 is a side view, partly in section, of an internal tissue puncture closure tool;

FIG. 2 is a side view of the tissue puncture closure tool of FIG. 1 inserted through an insertion sheath and engaged with an artery, the artery shown in section;

Figure 3:
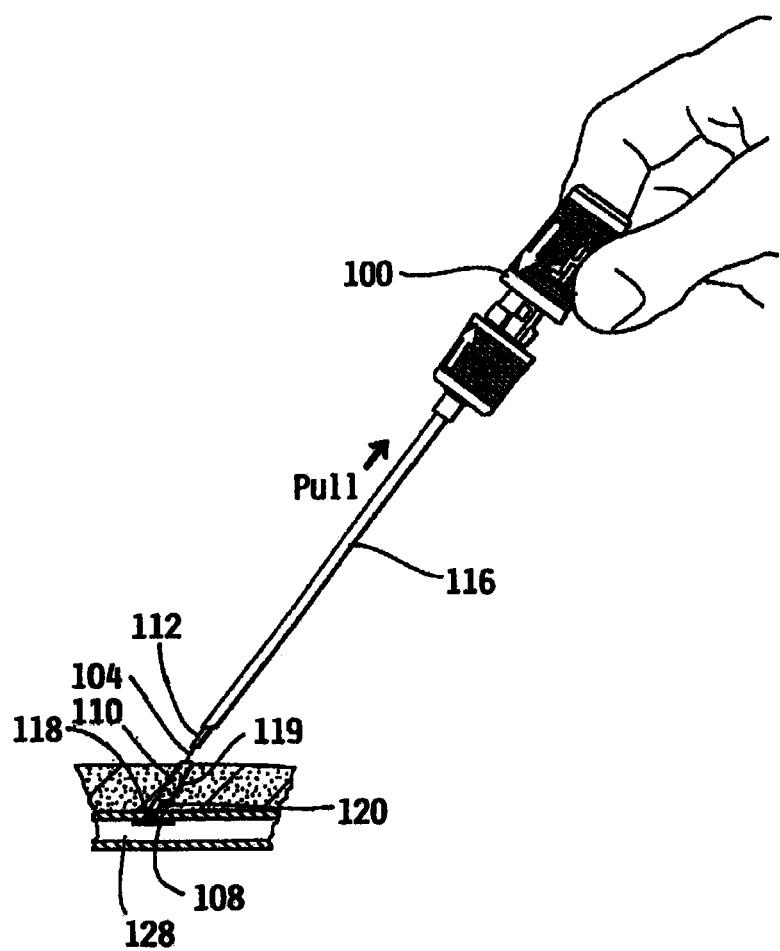
FIG. 3 is a side view of the tissue puncture closure tool, insertion sheath, and artery of FIG. 2, wherein the tissue closure tool and insertion sheath are being withdrawn from the artery to deploy a sealing plug, a collagen pad.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the disclosure is to cover all modifications, equivalents, and alternatives.

DETAILED DESCRIPTION

The present disclosure relates to an anchor that is configured to provide a bioresorbable seal to a tissue puncture, to an incision, and the like. The anchor is designed to provide the strength that is needed to seal the puncture or incision, and can also be tailored to resorb in the body over a specific desired timeframe. The present disclosure is directed to an anchor wherein the initial strength of the anchor and the bioresorption rate can be determined by the multiple materials used to make the anchor. For example, the initial strength of the anchor can be maintained or enhanced and, at the same time, the period of bioresorption can be maintained or reduced. Alternatively, the period of bioresorption could be extended, if the situation warranted such an extended bioresorption time.

Referring to the drawings, and in particular to FIGS. 1-4, a vascular puncture closure tool 100 is shown according to the prior art. The vascular puncture closure tool 100 includes a carrier tube 102 with a filament or suture 104 extending at least partially therethrough. The vascular puncture closure tool 100 also includes a first or proximal end 106 and a second or distal end 107. External to a second or distal end 107 of the carrier tube 102 is an anchor 108. The anchor, in this example, is an elongated, stiff, low profile member including an eye 109 formed at the middle. However, the anchor can vary in shape and stiffness. The anchor 108 is typically made of a biologically resorbable polymer.

The suture 104 is threaded through the anchor 108 and back to a sealing pad; for example, a collagen pad 110. The collagen pad 110 may be comprised of randomly oriented fibrous material bound together by chemical means. The collagen pad 110 is slidingly attached to the suture 104 as the suture passes distally through the carrier tube 102, but as the suture traverses the anchor 108 and reenters the carrier tube 102, it is securely slip-knotted proximal to the collagen pad 110 to facilitate cinching of the collagen pad 110 when the vascular puncture closure tool 100 is properly placed and the anchor 108 deployed (see FIG. 4).

The carrier tube 102 typically includes a compaction device, tamping tube or compaction tube 112, disposed therein. The compaction tube 112 is slidingly mounted on the suture 104 and may be used by an operator to tamp the collagen pad 110 toward the anchor 108 at an appropriate time to seal a percutaneous tissue puncture.

Prior to deployment of the anchor 108 within an artery, the eye 109 of the anchor 108 rests outside the distal end 107 of the carrier tube 102. The anchor 108 may be temporarily held in place flush with the carrier tube 102 by a bypass tube 114 disposed over the distal end 107 of the carrier tube 102.

Figure 4:
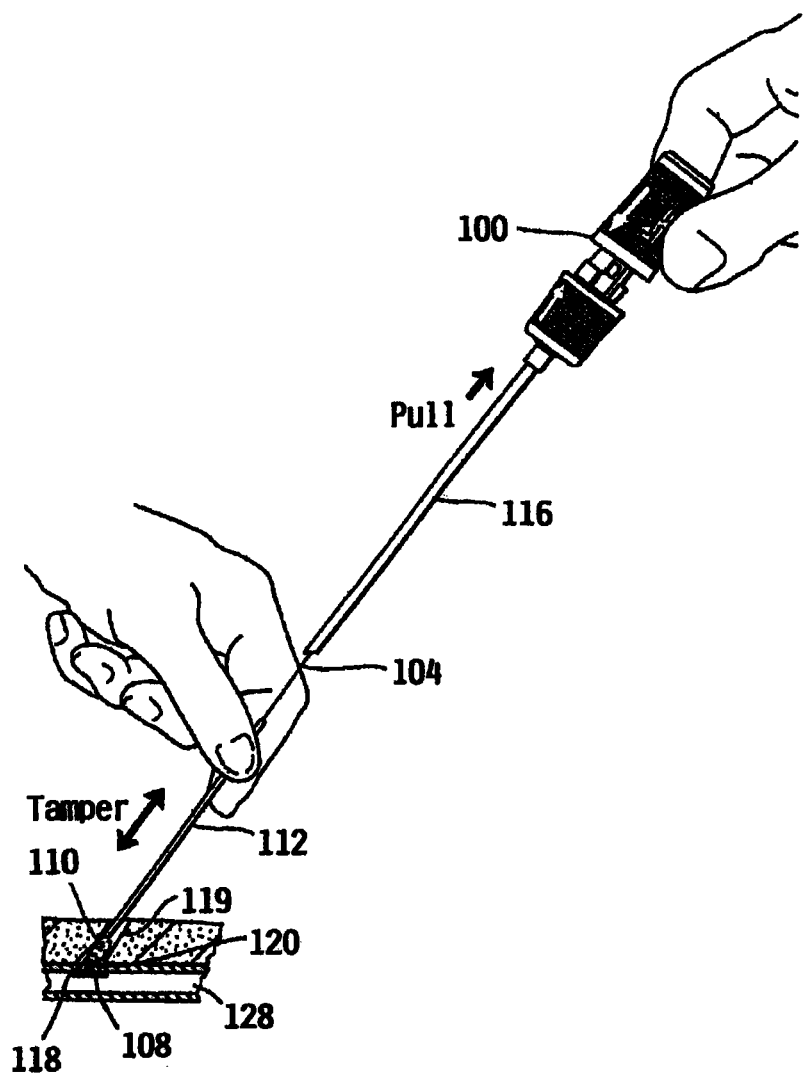
FIG. 4 is a side view of the tissue puncture closure tool, insertion sheath, and artery shown in FIG. 3 with a compaction device fully exposed and being used to tamp the collagen pad.

The flush arrangement of the anchor 108 and carrier tube 102 allows the anchor 108 to be inserted into an insertion sheath 116 as shown in FIGS. 2-4, and eventually through an arterial puncture 118. The insertion sheath 116 is shown in FIGS. 2-4 inserted through a percutaneous incision 119 and into an artery 128. However, the bypass tube 114 (FIG. 1) includes an oversized head 120 that prevents the bypass tube 114 from passing through an internal passage of the insertion sheath 116. Therefore, as the vascular puncture closure tool 100 is inserted into the insertion sheath 116, the oversized head 120 bears against a surface 122 of the insertion sheath 116. Further insertion of the vascular puncture closure tool 100 results in sliding movement between the carrier tube 102 (FIG. 1) and the bypass tube 114, releasing the anchor 108 from the bypass tube 114 (FIG. 1). However, the anchor 108 remains in the flush arrangement shown in FIG. 1 following release from the bypass tube 114 as the insertion sheath 116 continues to limit anchor 108 movement.

The insertion sheath 116 includes a monofold 124 at a second or distal end 126 thereof. The monofold 124 acts as a one-way valve to the anchor 108. The monofold 124 is a plastic deformation in a portion of the insertion sheath 116 that elastically flexes as the anchor 108 is pushed out through the distal end 126 thereof. Typically, after the anchor 108 passes through the distal end 126 of the insertion sheath 116 and enters the artery 128, the anchor 108 is no longer constrained to the flush arrangement with respect to the carrier tube 102 and it deploys and rotates to the position shown in FIG. 2.

Referring next to FIGS. 3-4, with the anchor 108 deployed, the vascular puncture closure tool 100 and the insertion sheath 116 are withdrawn together, forcing the collagen pad 110 through the tip of the carrier tube 102 and depositing it in the percutaneous incision 119. The compaction tube 112 is also exposed. With the compaction tube 112 fully exposed as shown in FIG. 4, the compaction tube 112 is manually grasped, the collagen pad 110 is manually tamped, and the anchor 108 and collagen pad 110 are cinched together and held in place with the self-tightening slip-knot on the suture 104. Thus, the tissue puncture is sandwiched between the anchor 108 and the collagen pad 110, thereby sealing the arterial puncture 118. The suture 104 is then cut and the percutaneous incision 119 may be closed. The suture 104, anchor 108, and collagen pad 110 are generally made of resorbable materials and therefore remain in place while the arterial puncture 118 heals.

Figure 5:
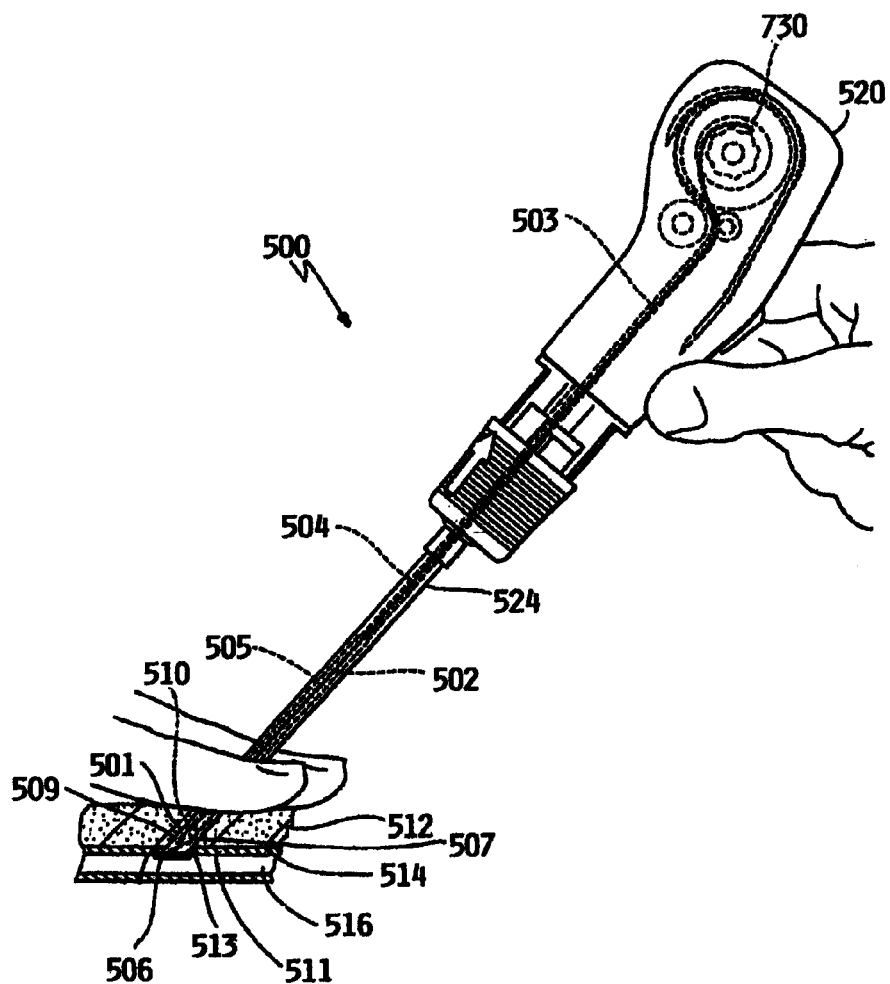
FIG. 5 is a side view of a tissue puncture closure tool with an automatic compaction mechanism shown engaged with an artery.
Figure 6:
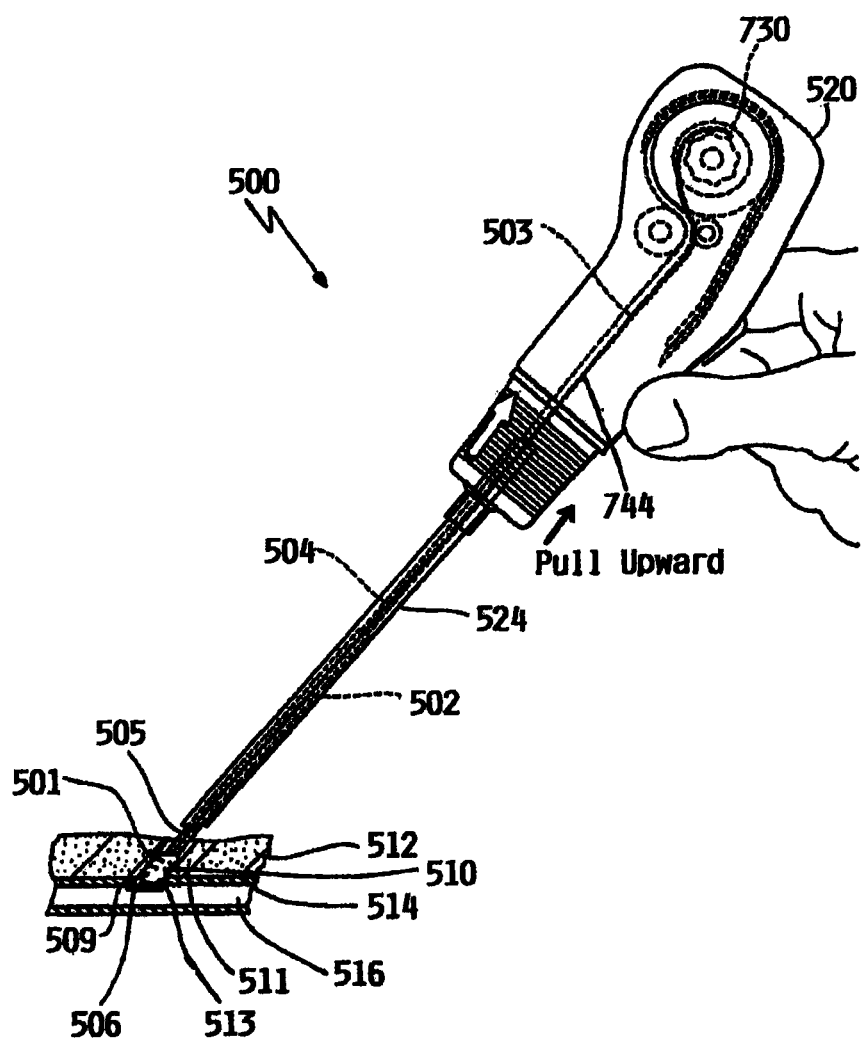
FIG. 6 is a side view of the tissue puncture closure tool of FIG. 5 being withdrawn from an artery.

Referring to FIGS. 5 and 6, there is shown another vascular puncture closure tool. The tissue closure tool 500 includes a first or proximal end 503 and a second or distal end 507. A carrier tube 504 extends from the proximal end 503 to the distal end 507 and includes a distal outlet. The carrier tube 504 may be made of plastic or other material and is designed for insertion through a sheath 524 which is designed for insertion through a percutaneous incision 501 in a tissue layer 512 and into a lumen 516. According to FIG. 5, the lumen 516 defines an interior portion of a femoral artery 514.

The distal end 507 of the carrier tube 504 also includes an anchor and a sealing plug 510. The anchor 506 is an elongated, stiff, low-profile member preferably made of a biologically resorbable polymer. However, other anchor shapes and flexibility are contemplated. The sealing plug 510 is formed of a compressible sponge or foam, made of a hemostatic biologically resorbable material such as collagen, and may be configured in any shape so as to seal the tissue puncture 513.

The sealing plug 510 and anchor 506 are connected to one another by a suture or filament 502 that is also biologically resorbable. The suture 502 extends distally from the first or proximal end 503 of the closure tool 500 through the carrier tube 504. The suture 502 is threaded through the sealing plug, then through a hole in the anchor 506 and proximally back through the carrier tube 504 to the sealing plug 510. The suture 502 is preferably threaded through a perforation or series of perforations in the sealing plug 510. The suture 502 may also be threaded around itself to form a slip-knot. The suture 502 thus connects the anchor 506 and the sealing plug 510 in a pulley-like arrangement that serves to cinch the anchor 506 and the sealing plug 510 together when the carrier tube 504 is pulled away from the anchor 506 and the sealing plug 510, locking the anchor and plug together and thereby sealing the tissue puncture 513.

The carrier tube 504 also includes a compaction device, such as a tamping tube 505, for tamping the sealing plug 510 along the suture 502 and against the anchor 506. The tamping tube 505 is shown located within the carrier tube 504 and proximal of the sealing plug 510. The tamping tube 505 is an elongated tubular member that may be rigid or flexible and formed of any suitable material. The suture 502 extends through the tamping tube 505 but is not directly connected thereto. Accordingly, the suture 502 and tamping tube 505 are free to slide past one another. According to the embodiment of FIG. 5, as the suture 502 extends beyond a proximal end of the tamping tube 505 and attaches to an automatic driving mechanism 730 located within a housing 520 at the first or proximal end 503 of the closure tool 500.

In practice, the carrier tube 504 of the closure tool 500 (containing the closure elements described above) is inserted into an insertion sheath 524, which is already inserted within the artery 514. As the closure tool 500 and the associated closure elements are inserted into the insertion sheath 524, the anchor 506 passes through and out of a distal end 509 of the insertion sheath 524 and is inserted into the lumen 516 of the artery.

The closure tool 500 is then withdrawn from the insertion sheath 524 until the anchor 506 catches on the distal end 509 of the insertion sheath 524 and rotates to the position shown in FIG. 5. When resistance to further retraction of the closure tool 500 is felt by an operator, the closure tool 500 and the insertion sheath 524 are withdrawn together, causing the anchor 506 to anchor itself within the artery 514 against the artery wall 511. With the anchor 506 anchored within the artery 514 at the site of tissue puncture 513, further retraction of the closure tool 500 and insertion sheath 524 causes the sealing plug 510 to withdraw from the distal end 507 of the carrier tube 504, thereby depositing the plug within the percutaneous incision or puncture tract 501.

However, unlike the initial closure tool described above, and similar such closure tools that require a separate, manual tamping procedure following the deposition of the sealing plug 510, closure tool 500 automatically tamps the sealing plug 510. The automatic driving mechanism 730 drives, via a rack or tamping tube driver 744, the tamping tube 505 toward the sealing plug 510 automatically upon withdrawal of the closure tool 500 from the puncture tract, tamping the plug toward the anchor 506 as shown in FIG. 6. The rack or compaction tube driver 744 can be coilable or can be a linear rack. Further, the rack, either coilable or not, can also function as the tamping tube, with the requisite column strength when the distal end of the rack is positioned adjacent the sealing plug 510. The sealing plug 510 is tamped while the carrier tube 504 is still arranged adjacent to the tissue puncture 513 in the femoral artery 514, reducing or eliminating any gaps that may otherwise occur between the sealing plug 510 and the tissue puncture 513 in the femoral artery 514.

In addition, by placing tension on or pulling the suture 502 away from the puncture tract, the suture 502 cinches and locks (with a slip knot or the like) together the anchor 506 and the sealing plug 510, sandwiching the artery wall 511 between the anchor 506 and sealing plug 510. The force exerted by the tamping tube 505 and the cinching together of the anchor 506 and sealing plug 510 by the suture 502 also causes the sealing plug 510 to deform radially outward within the puncture tract and function as an anchor on the proximal side of the site of the tissue puncture 513.

Applications of closure tools, including those implementing principles described herein, include closure of a percutaneous puncture or incision in tissue separating two internal portions of a living body, such as punctures or incisions in blood vessels, ducts or lumens, gall bladders, livers, hearts, etc.

Figure 7:
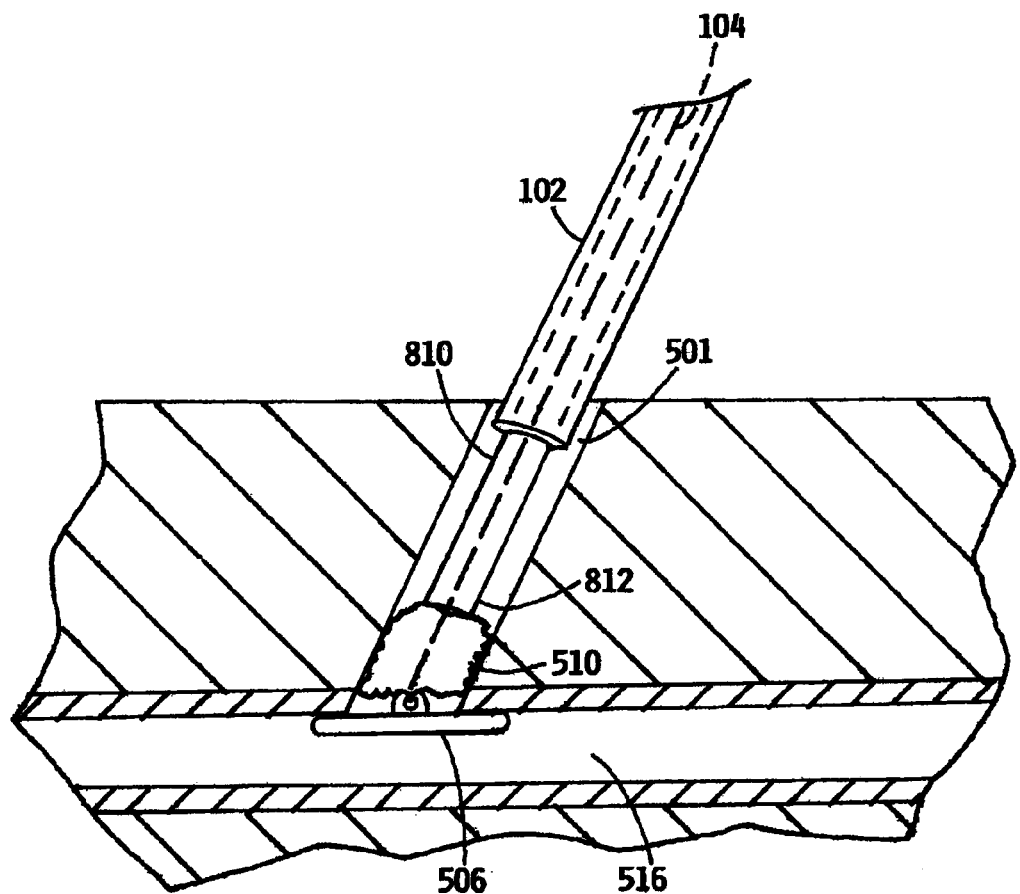
FIG. 7 is side view of an anchor deployed in a vessel, and a compaction tube inserted in an incision or puncture tract and tamping the sealing plug towards the anchor.

As noted in the above two examples of closure tools, in each case an anchor is deployed into a lumen, in particular, into an artery, and more particularly, into a femoral artery. Further, the closure tool can be used for closing punctures or incisions in various tissue, and the anchor used to provide a sealing surface can be sized for the particular puncture and tissue requirement. The anchor can take on various shapes, but generally is elongate with a longitudinal axis and has a width with a lateral axis. However, the anchor can take on a number of different shapes and profiles suitable to cover the opening in the vessel or tissue. The anchor is dimensioned to at least cover the opening the anchor is meant to seal. The anchor generally includes an attachment structure whereby the anchor can be positioned and held securely against the puncture or incision opening that is to be sealed. The attachment structure can include at least one or a plurality of lateral passages in the top surface of the anchor, the passages adapted to receive a connecting means such as a thread or filament. Alternatively, the anchor can include a centrally positioned loop on the top surface of the anchor. The top surface of the anchor is defined as the surface of the anchor that is in contact with the puncture opening and the tissue/wall surrounding the opening. Other attachment configurations are contemplated. The thread or filament connects the anchor through the puncture tract to the opposite side of the tissue/wall opening. As noted above, a sealing plug, such as a collagen plug can be connected to the anchor by way of a thread or filament, positioning the sealing plug in the puncture tract and assisting in holding the anchor in place. A separate locking device or knot can be used to keep the sealing plug and anchor positioned relative to one another, sandwiching the tissue/wall with the opening, thus sealing the opening. FIG. 7 shows an example of a percutaneous incision or puncture tract 501 and artery 516, with a closure tool implanting an anchor 506 through an opening in a vessel wall.

The closure tool, as noted above, can be used to close punctures or incisions in various tissue and vessels. The stresses that the anchor can be subjected to can vary dependent upon the position of the anchor in the body. For example, an anchor used in a gallbladder procedure can undergo different stress as compared to an anchor used in sealing a puncture in an artery. Hence, an anchor can be designed to provide the particular characteristics best suited for the location of the anchor in the body, for the stresses that the anchor may be subjected to, and for the desired resorbtion rate for the anchor. The closure tool, including the anchor, can be used to close various punctures and incisions, and the composition and structure of the anchor may, as a result, vary. The closure of an opening in a vessel wall is provided by way of a non-limiting example of demonstrating one embodiment of the disclosure.

In one embodiment, the anchor of the present disclosure can be made of a material or combination of materials that provide the desired resorption time and anchor strength for use in sealing an opening in a vessel wall. An insertion sheath or other device is used to initially insert the anchor in the tissue puncture or incision, and the anchor is inserted in the blood vessel. The anchor is positioned against an interior surface of the vessel wall where the top surface of the anchor abuttingly engages the interior surface of the vessel wall, and in particular, abuttingly engages the interior surface of the vessel wall at the opening in the vessel wall. FIG. 7 shows an anchor in place in a vessel, sealing an opening in the wall of the vessel. As noted above, a sealing plug, such as a collagen plug, can be positioned at the exterior surface of the vessel wall, in the puncture tract. The collagen sponge and anchor are compressed together by way of a suture or filament, thus sealing the opening and facilitating rapid healing. The anchor eventually resorbs into the body, generally over a period of 1-2 months.

In this embodiment of the disclosure, it is desired that the anchor not bend when it is positioned during initial implantation and that it does not weaken too quickly, as the anchor is required to provide a seal at the interior surface of the wall of the vessel. In this position at the interior surface of the wall of the vessel, as shown in FIG. 7, the anchor must remain intact, and slowly resorb or "melt away", with no pieces possibly coming loose and entering the blood stream. Further, it is desirable that the anchor initially maintain its strength and integrity so that the opening in the vessel can begin to heal, prior to the anchor beginning to weaken and resorb into the body. Hence, the anchor used in sealing an opening in a vessel can be designed to provide the initial strength desired and the resorption rate desired through the use of different materials and overmolding or coating (for example, spray coating, spin coating, dip coating, thin film coating, and vapor deposition coating) various specific aspects of the anchor.

Generally, the anchor can be made of a bioresorbable polymer that is typically absorbed by the body in 1-2 months. The polymer structure can be amorphous and the properties of the anchor include a glass transition temperature that is close to the temperature of the body. The bioresorbable polymer generally tends to degrade and/or swell when in contact with bodily fluid and, subsequently, structurally weakens. In one embodiment, the polymer can degrade via hydrolysis and/or may swell as it degrades. Although it is desirable that the anchor eventually become structurally weak and resorb in the body, it is also desirable that the anchor maintains its original strength for about 2-7 days until the body has had a better chance to begin healing itself. Therefore, the entire anchor, or only specific portions of the anchor, can be overmolded or coated with another material, to provide strength to the anchor and also allow the anchor to resorb in the desired time frame.

In another embodiment, the inner anchor material provides mechanical strength while the outer anchor material controls the degradation rate of the entire component. The outer anchor material is the material in direct contact with blood and tissues.

Bioresorbable materials, for example, PEG (polyethylene glycol) hydrogel materials, PGA (polyglycolytic acid), PLGA (copoly lactic acid/glycolic acid), PDLG (50/50 DL-Lactide/glycolide copolymer), polyhydroxybutyrate, DL-lactide/L-lactide, triemethylene carbonate, para-dioxanone and ε-caprolactone copolymers, lactide polymer, glycolide polymer, and the like, can be used as material for the inner anchor. Other bioresorbable material alternatives for the inner anchor material are, for example, polyanhydrides, polyvinylalcohol, polyorthoesters, and polycarbonates. In addition, all the above materials can be combined into block-polymers as desired to adjust material properties. The inner anchor material can also be made from a variety of water soluble monosaccharides or disaccharides (sugars) consisting of, or a blend of, or a chemical combination of fructose, glucose, galactose, and mannose, sucrose, lactose, pectin, dextrose or other sugar-based products, as well as carbohydrates, such as alginate, chitosan, and hyaluronic acid. The inner anchor material can also be made from water soluble salts, such as NaCl, KCl, $CaCl_2$, and $MgCl_2$, or water soluble oxyhydroxides, such as hydroxides, phosphates, carbonates, and mixes thereof or a biodegradable metal, such as magnesium or magnesium alloy. The inner anchor material can be selected from a salt or compounds containing iodide or bromide to promote radioopacity of the anchor.

The choice of the inner anchor material can depend on a number of performance characteristics, such as speed of resorption, flexibility, and thermal conductivity. Generally, bodily fluids, for example, blood and fluids contained in tissue, are in contact with the anchor. Without being bound to a particular theory, the fluids act as a plasticizer when in contact with the polymer material of the anchor and, as a result, the anchor begins to degrade and resorb. For example, a PEG hydrogel material can be used for the anchor structure. The PEG hydrogel inner anchor will degrade and swell somewhat when it is in contact with liquid, such as water, and bodily fluids. It is desirous that the anchor swells, to some extent, to create pressure on the internal portion of the puncture or incision, to aid in holding the sealant plug in place and assist in the healing process. Further, it is desirable that the anchor swell preferentially in one direction, towards the interior surface of the vessel wall, to apply pressure to the interior surface of the vessel wall at the opening and thus to the sealing plug. Although, the anchor should not degrade or swell too quickly, at least initially, or the anchor may become weakened and potentially bend into the lumen, or otherwise allow the seal to leak.

In one embodiment, a second material can be overmolded onto the exterior of the anchor, now forming an inner anchor structure (e.g. the inner PEG anchor), and an outer anchor structure. The combination of materials provides the required initial anchor strength and resorption rate. In another embodiment, the second material can be coated on, as described below.

For water soluble polymers, organic and inorganic materials, water can act as a solvent for the material. For example, a disaccharide can be pressed or sintered into the desired anchor shape and act as the inner anchor structure. This hard inner structure is beneficial for securing the attachment of the suture to the anchor and to maintain the suture attachment until, at least, the anchor has been covered by tissue. The inner structure is coated with an outer material structure that temporary hinders the penetration of water to the inner, structure-providing material. The outer material is softer compared to the inner material to provide optimal tissue and blood interactions of the structure.

Figure 8:
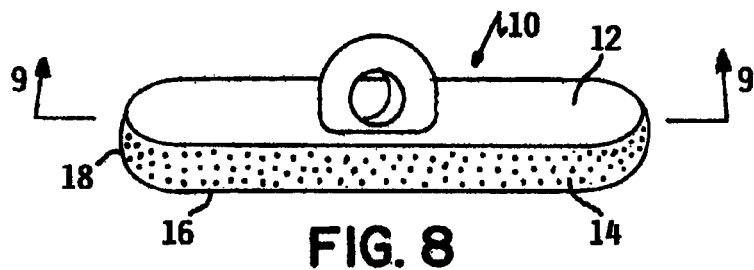
FIG. 8 is a perspective view of an anchor according to one aspect of the disclosure.
Figure 9:
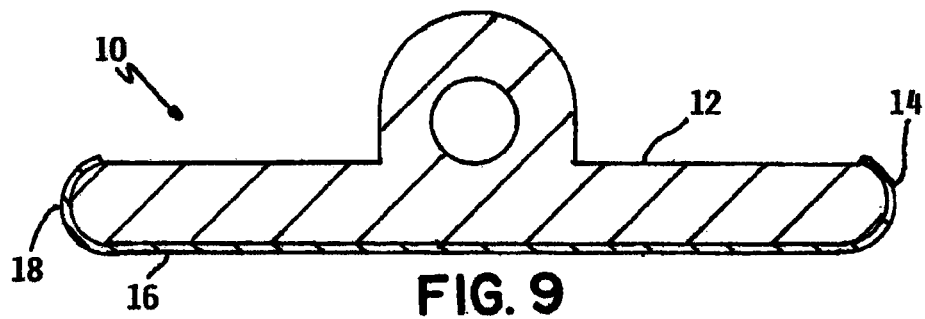
FIG. 9 is a cross-sectional view of the anchor of FIG. 8.

The following figures, although referencing an overmolded anchor, can also represent an anchor that is coated with another material. FIGS. 8-9 show one embodiment of the disclosure whereby an anchor 10 is overmolded with another overmold material 14, where the overmold material 14 is limited to the sides and bottom surface of the anchor 10; the surface of the anchor that is in direct contact with the bloodstream. FIG. 9 is a cross-sectional view of the anchor 10 of FIG. 8, where the inner anchor 12 is shown with the overmold material 14 molded onto the bottom surface 16 and side surfaces 18 of the anchor 10. The overmold material 14 can delay bodily fluid accessing the inner anchor 12 and, therefore, the beginning of the resorption process. Instead, the overmold material 14 can react more slowly to the fluid content of the blood, thus protecting the inner anchor 12 for a number of days, so that the opening can begin to heal with the anchor 10 firmly in place against the opening. After, for example, 2-7 days, the overmold material 14 can begin to resorb, thus allowing some access of bodily fluid, for example, the water present in various bodily fluids, to the inner anchor 12 to begin the general resorption process. Without the overmolded areas, the anchor 10 would immediately begin the resorption process. Alternatively, instead of the overmold material 14 beginning to resorb after about 2-7 days, the overmold material 14 can be less hydrophilic and allow water to penetrate the overmold material 14, but at a slower rate, thereby slowing plasticization and resorption of the inner anchor. Once the overmold material 14 has begun to be resorbed, the resorption rate of the anchor 10 can be accelerated, if desired, due to the nature of the material of the inner anchor 12. Additionally, the surface of the inner anchor 12 can be designed with increased surface area, for example, by roughing the surface or putting undulations in the surface, thereby facilitating an increased resorption rate. Further, a roughened surface of the inner anchor 12 can assist in bonding the overmold material 14 to the inner anchor 12. Alternatively, instead of a more rapid resorbtion rate, the inner anchor 12 can have a similar resorption rate as the overmold material 14. Further, the inner anchor 12 material can be more flexible or have other characteristics that are desirable at this point of the healing process.

Figure 10:
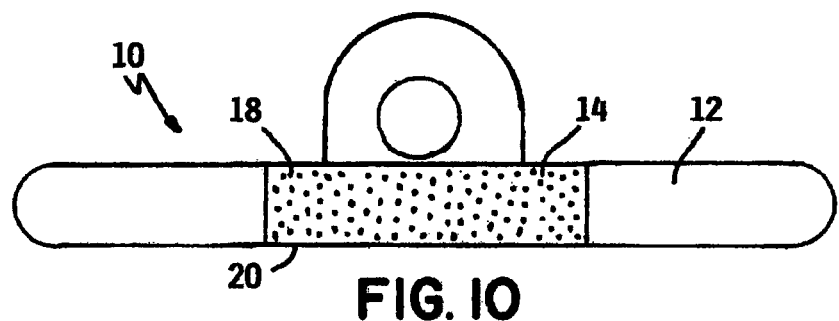
FIG. 10 is a side view of an anchor according to one aspect of the disclosure.
Figure 11:
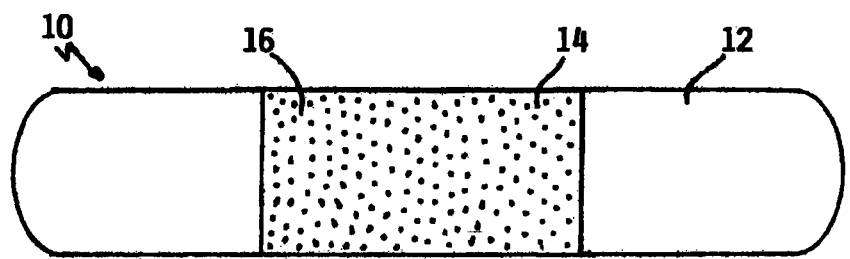
FIG. 11 is a bottom view of the anchor of FIG. 10.
Figure 12:
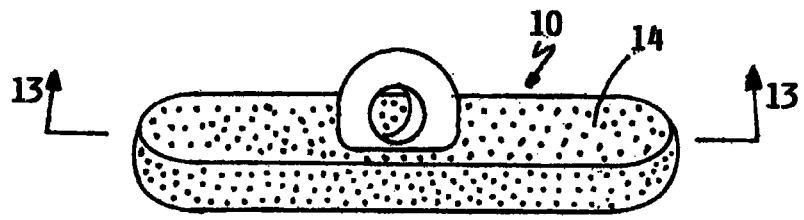
FIG. 12 is a perspective view of an anchor according to one aspect of the disclosure.
Figure 13:
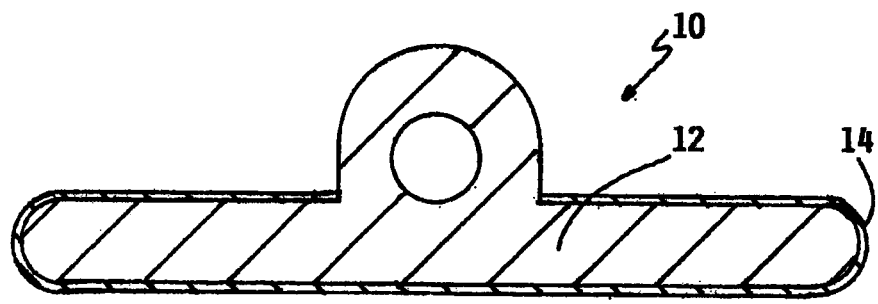
FIG. 13 is a cross-sectional view of the anchor of FIG. 12.
Figure 14:
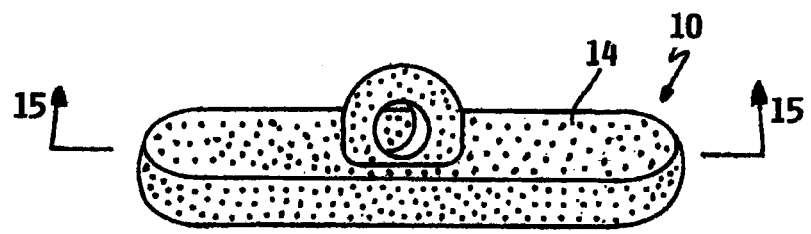
FIG. 14 is a perspective view of an anchor according to one aspect of the disclosure.
Figure 15:
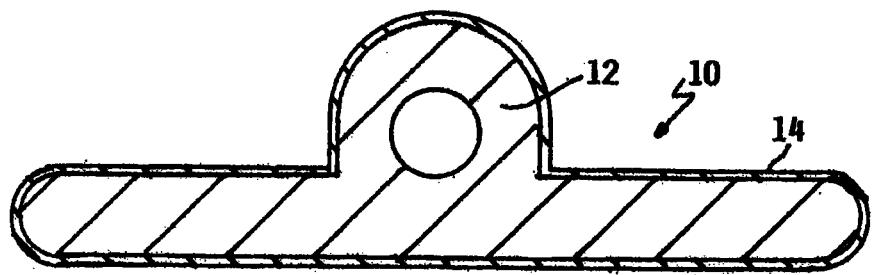
FIG. 15 is a cross-sectional view of the anchor of FIG. 14.
Figure 16:
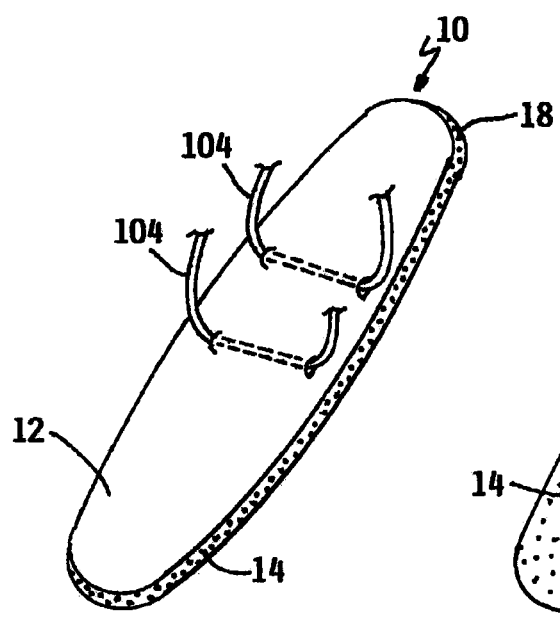
FIG. 16 is a perspective planar view of an anchor according to one aspect of the disclosure.
Figure 17:
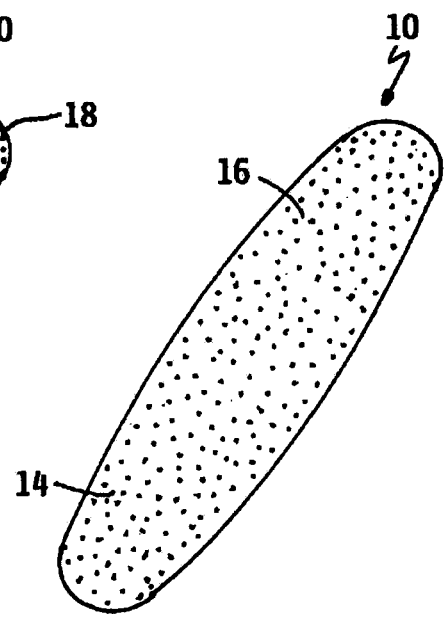
FIG. 17 is a bottom view of the anchor of FIG. 16.
Figure 18:
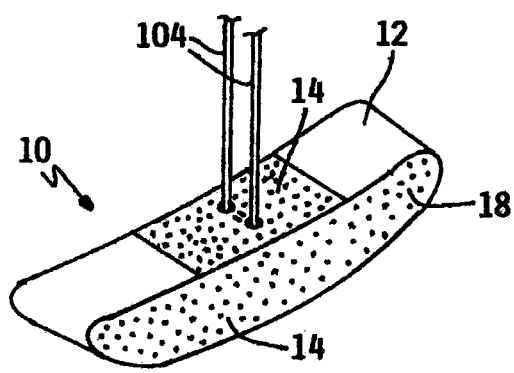
FIG. 18 is a perspective view of an anchor according to one aspect of the disclosure.

In another embodiment of the disclosure, as shown in FIG. 10, a central segment 20 of the anchor 10 is overmolded. The bottom surface 16 and the side surfaces 18 of the central segment 20 are overmolded with a material different as compared to the rest of the anchor 10. The central segment 20 of the anchor 10 tends to be subjected to the greatest amount of bending stress. Hence, an overmold material 14 to this area of the anchor can provide the strength, integrity and delayed initial resorption that is desired in the anchor 10. However, once the overmolded central segment 20 has begun the resorption process, a faster resorbing material can be used in the rest of the inner anchor 12 to increase the overall speed of anchor 10 resorption. FIG. 12 shows another embodiment of the disclosure, whereby the entire anchor 10 is overmolded with a resorbing material, except for the ring or attachment point for the filament, thread or suture. FIG. 13 is a cross-sectional view of the anchor shown in FIG. 12. The overmold material 14 can vary as to resorption speed, as compared to the material of the inner anchor, dependent upon the needs of the particular application. FIG. 14 shows another embodiment of the disclosure, whereby the entire anchor 10 is overmolded with a resorbing material. Consideration can be given to the nature of the overmold material 14, for example, hardness/softness of the overmold material 14, when the attachment point of the anchor is also overmolded. With a filament or the like threaded through the hole in the attachment ring or loop, the filament can have a tendency to rub and potentially to cut into the surface of the ring. Hence, various characteristics of the overmold material 14 can be considered with respect to performance needs, when contemplating which portions of the anchor to overmold. Dependent upon the use, placement, and requirements of the anchor 10, the anchor 10 can be selectively, partially or completely overmolded or coated to provide the desired performance. Further, the choice of materials for the inner anchor 12 and for the overmold material 14 can provide the various characteristics desired for a particular anchor 10 usage, including relative resorption rates, flexibility and strength. Additional example structures of anchors are provided in FIGS. 16-18, and other anchor structures are contemplated. Like numerals refer to like structure in the figures.

As noted above, the anchor 10 can be generally made of a bioresorbable material, for example, PEG (polyethylene glycol) hydrogel materials, PGA (polyglycolytic acid), PLGA (copoly lactic acid/glycolic acid), PDLG (50/50 DL-Lactide/glycolide copolymer), polyhydroxybutyrate, DL-lactide/L-lactide and ϵ-caprolactone copolymers, triemethylene carbonate, para-dioxanone, lactide polymer, glycolide polymer, water soluble sugar-based products, salts oxyhydroxides, such as hydroxides, phosphates, carbonates, and mixes thereof or a biodegradable metal, and the like. In one embodiment, the anchor 10 can be made using a two-stage injection molding process. In a two-stage injection molding process, one of the above materials or the like can be used in the first shot of the molding process, thus forming the inner anchor 12. The first stage or inner anchor 12 is dimensionally smaller than the final anchor 10, and can be similar in shape, but not necessarily. After the inner anchor 12 is molded, a second overmold material 14 is overmolded on the material of the inner anchor 12. The second shot in the two-stage injection molding process can be a complete overmold of the overmold material 14 over the entire structure of the inner anchor 12, or over only a selected portion or portions of the inner anchor 12. The second shot of the two-stage injection molding process can be a selective overmold of the overmold material 14 that reinforces and/or slows the resorption process for certain segments of the anchor 10. To achieve the same end, instead of selectively overmolding the inner anchor 12, the entire anchor 10 can be overmolded and then selective areas of the overmold material 14 can be removed to obtain the desired structure of the anchor 10. Materials that can be used for the second shot (the overmold material) include, for example, poly (L-lactides), poly (DL-lactides), polyglycolides, L-lactide/DL-lactide copolymers, polyethylene glycol, PEG hydrogels, L-lactide/glycolide copolymers, glycolide/caprolactone/lactides, gelatin coatings, magnesium metal, biodegradable iron or iron alloys, manganese or manganese based alloys, pyrolytic carbon, expanded PTFE (polytetrafluoroethylene), biocompatible fabrics or textiles (for example, Dacron®; polyethylene terephthalate), tyrosine-derived polycarbonates, and the like.

In another embodiment, a thin conformal coating can be applied to the inner anchor 12, or sections of the inner anchor 12. Generally, the conformal coating of the overmold material 14 takes the place of the two-stage injection overmold of the overmold material 14 and functions similarly to the overmold material 14. For example, pyrolytic carbon, hydroxyaptite, and the like can be applied as a thin conformal coating by, for example, dip coating, spin coating, spray coating, thin film coating, vapor deposition, or other MEMS processes. From a production/manufacturing process view, instead of overmolding selected portions of the inner anchor 12 or applying a conformal coating to selected portions of the inner anchor 12, the entire inner anchor 12 can be overmolded/coated and then the overmold material 14 (also referred to as a coating 14) can be selectively removed, leaving portions of the inner anchor 12 surface exposed. The anchors shown in FIGS. 8-18 could be overmolded or coated.

The various combinations and permutations of inner anchor material, overmold or coating material, and selected area(s) of overmolding/coating the anchor 10, can provide the characteristics desired in an anchor 10 or other sealing component. While the anchor 10 has been shown in use with vascular instruments described above, the application of principles described herein are not limited to the specific devices shown. The principles described herein may be used with any vascular or tissue closure device. Therefore, while the anchor 10 and use of the anchor 10 in the description above are directed primarily to arterial procedures and certain embodiments of a vascular closure device, it will be appreciated that the teachings of the present disclosure are applicable to other applications as well.

The preceding description has been presented only to illustrate and describe example embodiments of the disclosure. It is not intended to be exhaustive or to limit the disclosure to any precise form disclosed. Many modifications and variations are possible in light of the above teaching. Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the disclosure be defined by the attached claims and their legal equivalents.

What is claimed is:

1. A bioresorbable anchor for deployment in a live body, the anchor comprising:
   an inner anchor comprising a first bioresorbable material, the inner anchor comprising a top surface, a side surface, and an end portion; and
   an outer anchor comprising an overmold material, the overmold material comprising a second bioresorbable material;
   wherein a first portion of the top surface of the inner anchor and at least a portion of the side surface of the inner anchor are enveloped by the overmold material of the outer anchor;
   wherein a second portion of the top surface of the inner anchor and the end portion of the inner anchor are not enveloped by the overmold material of the outer anchor.

2. The anchor of claim 1 wherein the first bioresorbable material has a faster resorbtion rate than the second bioresorbable material.

3. The anchor of claim 1 wherein the second bioresorbable material is less hydrophilic than the first bioresorbable material.

4. The anchor of claim 1 wherein the first bioresorbable material is the same as the second bioresorbable material.

5. The anchor of claim 1 wherein the inner anchor is formed by a process selected from the group consisting of injection-molding, tablet pressing and sintering.

6. The anchor of claim 5 wherein the outer anchor is formed by a process selected from the group consisting of injection-molding material over the inner anchor and coating the inner anchor.

7. The anchor of claim 1 wherein the outer anchor is formed by coating the second bioresorbable material onto the inner anchor.

8. The anchor of claim 7 wherein the second bioresorbable material is coated onto the inner anchor by using a coating process selected from the group consisting of spin coating, dip coating, thin film coating, and vapor deposition coating.

9. The anchor of claim 1 wherein the first bioresorbable material is selected from the group consisting of PEG (polyethylene glycol) hydrogel materials, PDLG (50/50 DL-Lactide/glycolide copolymer), DL-lactide/L-lactide and ϵ-caprolactone copolymers, triemethylene carbonate, para-dioxanone, lactide polymer, glycolide polymer, polyanhydrides, polyorthoesters, polycarbonates, water soluble monosaccharides, water soluble disaccharides, water soluble salts, water soluble oxyhydroxides, and water soluble oxyhydroxides mixed with magnesium or magnesium alloy.

10. The anchor of claim 1 wherein the second bioresorbable material is selected from the group consisting of poly (L-lactides), poly (DL-lactides), polyglycolides, L-lactide/DL-lactide copolymers, polyethylene glycol, PEG hydrogels, L-lactide/glycolide copolymers, glycolide/caprolactone/lactides, gelatin coatings, pyrolytic carbon, expanded PTFE (polytetrafluoroethylene), biocompatible fabrics or textiles, and tyrosine-derived polycarbonates.

11. A bioresorbable anchor for deployment in a live body, comprising:
- a top surface;
- a bottom surface;
- side surfaces;
- an attachment device;
- a central portion positioned intermediate two end portions of the anchor, the attachment device being positioned on the top surface at the central portion;
- wherein the anchor comprises a first bioresorbable material and a second bioresorbable material, the second bioresorbable material being partially overmolded onto the first bioresorbable material, wherein at least portions of the top and side surfaces of the anchor have the second bioresorbable material externally exposed, and at least some portions of the top surface and end portions of the anchor have the first bioresorbable material externally exposed.

12. The anchor of claim 11 wherein the second bioresorbable material is externally exposed at the central portion of the anchor.

13. The anchor of claim 11 wherein the portions of the side surfaces that have the second bioresorbable material externally exposed include an entirety of at least one of the side surfaces.

14. The anchor of claim 11 further comprising at least one opening formed in the top surface, the at least one opening being configured to receive a suture.

15. The anchor of claim 11 wherein a resorption rate of the first bioresorbable material is different as compared to a resorption rate of the second bioresorbable material.

16. The anchor of claim 11 wherein a resorption rate of the first bioresorbable material is faster than the resorption rate of the second bioresorbable material.

17. The anchor of claim 11 wherein the second bioresorbable material provides additional strength to the anchor.

* * * * *